United States Patent
Klein

(10) Patent No.: US 6,849,775 B2
(45) Date of Patent: Feb. 1, 2005

(54) METHOD OF FORMING ABSORBENT PAD USING PRECUT OVERLAY

(76) Inventor: Jeffrey A. Klein, 30280 Rancho Viejo Rd., San Juan Capistrano, CA (US) 92675

( * ) Notice: Subject to any disclaimer, the term of this patent is extended or adjusted under 35 U.S.C. 154(b) by 73 days.

(21) Appl. No.: 10/434,644

(22) Filed: May 9, 2003

(65) Prior Publication Data

US 2004/0225248 A1 Nov. 11, 2004

(51) Int. Cl.$^7$ .................................................. A61F 5/00
(52) U.S. Cl. .............................. 602/41; 602/43; 602/47
(58) Field of Search .............................. 602/41, 43, 47

(56) References Cited

U.S. PATENT DOCUMENTS

| | | |
|---|---|---|
| 808,433 A | 12/1905 | Cartledge |
| 3,157,178 A | 11/1964 | Bentov |
| 3,279,465 A | 10/1966 | Cherio et al. |
| 3,824,996 A | 7/1974 | Carlisle |
| 3,871,378 A | 3/1975 | Duncan et al. |
| 3,888,248 A | 6/1975 | Moore et al. |
| 3,929,135 A | 12/1975 | Thompson |
| 3,967,623 A | 7/1976 | Butterworth et al. |
| 3,968,803 A | 7/1976 | Hyman |
| 4,282,874 A | 8/1981 | Mesek |
| 4,341,216 A | 7/1982 | Obenour |
| 4,347,844 A | 9/1982 | Ohki et al. |
| 4,400,832 A | 8/1983 | Kinder |
| 4,645,500 A | 2/1987 | Steer |
| 4,665,909 A | 5/1987 | Trainor |
| 4,681,577 A | 7/1987 | Stern et al. |
| 4,829,987 A | 5/1989 | Stewart |
| 4,835,795 A | 6/1989 | Lonon |
| 4,937,273 A | 6/1990 | Okayama et al. |
| 5,009,652 A | 4/1991 | Morgan et al. |
| 5,054,129 A | 10/1991 | Baehr |
| 5,060,315 A | 10/1991 | Ewing |

(List continued on next page.)

FOREIGN PATENT DOCUMENTS

FR          2519865          7/1983

OTHER PUBLICATIONS

Jeffrey Alan Klein, MD; The Tumescent Technique Anesthesia and Modified Liposuction Technique Dermatologic Clinic; vol. 8, No. 3, Jul. 1990.
Jeffrey A. Klein, M.D.; "The Tumescent Technique for Lipo–Suction Surgery", The American Journal of Cosmetic Surgery; vol. 4, No. 4, 1987.

(List continued on next page.)

*Primary Examiner*—Michael A. Brown
(74) *Attorney, Agent, or Firm*—Stetina Brunda Garred & Brucker

(57) ABSTRACT

A method of forming a generally leak-proof peripherally sealed absorbent pad and a pad formed by such method are disclosed herein. Non-sealed layered pads are formed by assembling the following layers: (1) a sheet of liquid-impermeable material; (2) bibulous pads disposed on the sheet of liquid-impermeable material, the bibulous pads disposed relative to each other based on a predetermined spacing; (3) a liquid-permeable sheet disposed on top of the bibulous pads; and (4) a sheet of liquid-impermeable material having precut apertures disposed on the liquid-permeable sheet, the apertures sized and shaped to be framed by the pads and spaced relative to each other based on the predetermined spacing. The non-sealed layered pads are then sealed along a periphery of the precut apertures to the sheet of liquid-impermeable material to form a sheet of absorbent pads. The sheet of absorbent pads are then cut proximate sealed edges of the precut apertures to form a plurality of generally leak-proof peripherally sealed absorbent pads.

19 Claims, 2 Drawing Sheets

U.S. PATENT DOCUMENTS

| | | |
|---|---|---|
| 5,281,208 A | 1/1994 | Thompson et al. |
| 5,348,547 A | 9/1994 | Payne et al. |
| 5,352,217 A | 10/1994 | Curro |
| 5,429,593 A | 7/1995 | Matory |
| 5,449,352 A | 9/1995 | Nishino et al. |
| 5,478,335 A | 12/1995 | Colbert |
| 5,681,579 A | 10/1997 | Freeman |
| 6,162,960 A | 12/2000 | Klein |

OTHER PUBLICATIONS

Jeffrey A. Klein, M.D.; "Tumescent Technique for Regional Anesthesia Permits Lidocaine Doses of 35 mg/kg for Liposuction"; J. Dermatol. Surg. Oncol 16:3; Mar. 1990.

Jeffrey A. Klein, M.D.; "Tumescent Technique for Local Anessthesia Improves Safety in Large–Volume Lipsuction"; The American Society of Plastic and Reconstructive Surgeons: Nov. 1993.

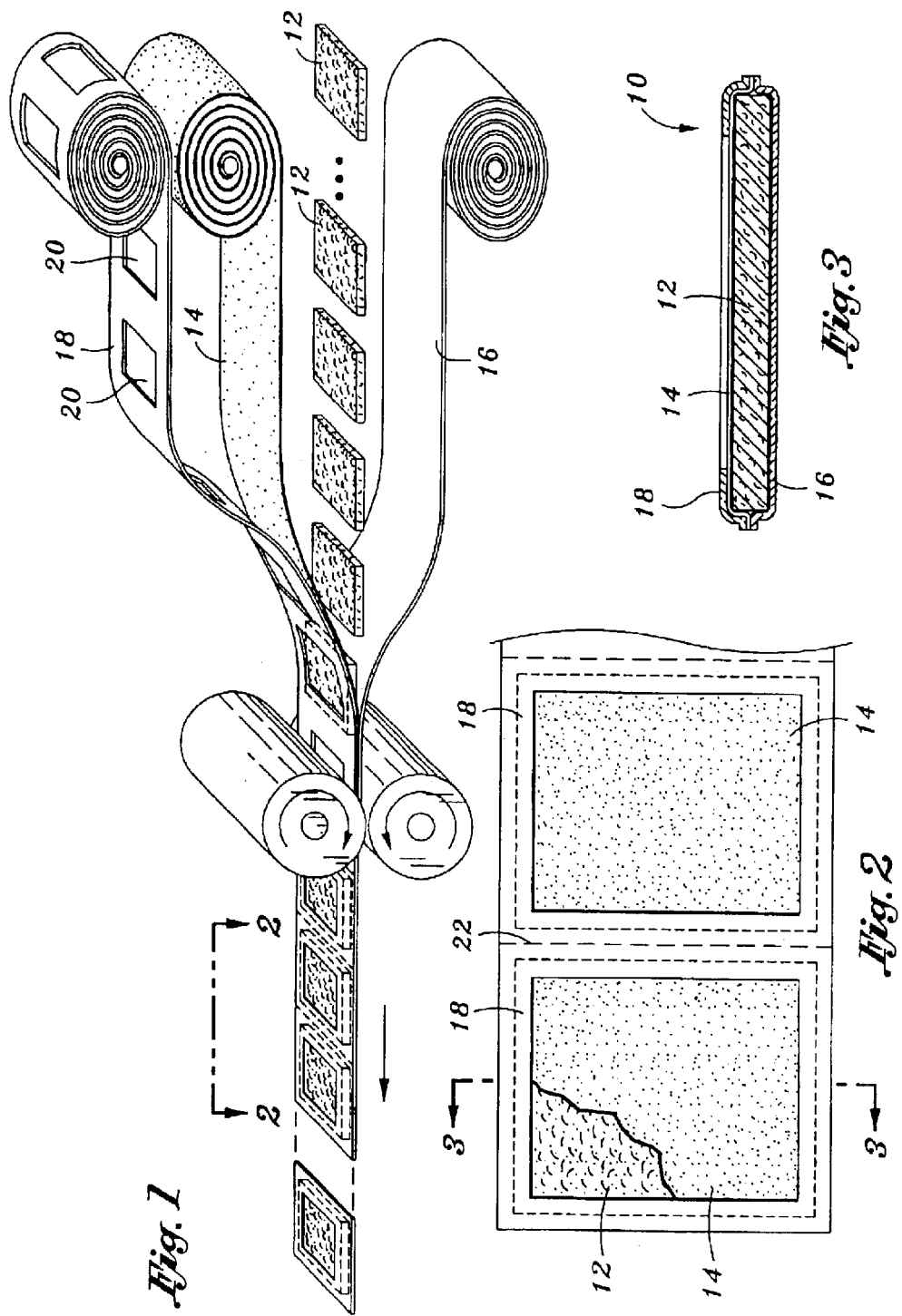

METHOD OF FORMING ABSORBENT PAD USING PRECUT OVERLAY

CROSS-REFERENCE TO RELATED APPLICATIONS

Not Applicable

STATEMENT RE: FEDERALLY SPONSORED RESEARCH DEVELOPMENT

Not Applicable

BACKGROUND OF THE INVENTION

The present invention relates in general to absorbent pads, and in more particular, to a method of forming a generally leak-proof peripherally sealed absorbent pad, such as a compression sponge for wound care, using a precut overlay.

Absorbent pads are known in the medical field. For example, U.S. Pat. No. 6,162,960, entitled COMPRESSION SPONGE FOR WOUND CARE, describes a highly absorbent pad that is ideally suited for use as a compression sponge for wound care. Absorbent pads, such as the one described in U.S. Pat. No. 6,162,960 have many uses. For example, such pads can be used for patient recovery from tumescent liposuction procedures involving infusion of relatively large quantities of liquid which must then exit incision sites. In such liposuction procedures, an elastic garment may be worn over an absorbent medium, but non-uniform distribution of absorbed liquid drainage in such cases can cause bruising of skin tissue.

The wound care sponge described in U.S. Pat. No. 6,162,960 includes a highly absorbent generally uniform bibulous layer which operates as a wick to absorb, generally uniformly distribute therethrough, and retain liquid whereby the uniform liquid distribution throughout the entire layer provides uniform pressure distribution of any externally applied pressure on the pad. A liquid-permeable sheet, such as a non-interacting liquid-permeable paper product is disposed on the surface of the bibulous layer to interface with the wound site. A liquid-impermeable sheet with wrap-around edges prevents leakage of liquid from the pad.

A typical method of manufacture of absorbent pads such as the one described in U.S. Pat. No. 6,162,960 involves using a large roller to assemble the layers of the pad. Layers are formed as follows: (1) a sheet of liquid-impermeable material; (2) precut pads of the bibulous material are disposed on the sheet of liquid-impermeable material; and (3) a sheet of liquid-permeable material is then disposed on the precut pads of the bibulous material. The three layers are then assembled using the large roller. After being assembled using the large roller, the edges of the liquid-impermeable material are manually wrapped around the pad to form a frame around the liquid-permeable material. The edges of the liquid-impermeable material are then sealed to the liquid-permeable material. Such a manual process is time-consuming and costly.

Thus, a need exists for a more efficient, less labor intensive method of forming a generally leak-proof peripherally sealed absorbent pad.

In addition to the problems described above, many prior art absorbent pads are sealed only on two or three sides. Such pads are not sufficient for many applications. In particular, such pads are generally not suitable for uses in which the pad will be in a vertical orientation.

Thus, there is also a need for a more efficient, less labor intensive method of forming a generally leak-proof peripherally sealed absorbent pad that is sealed around all of the edges of the pad.

BRIEF SUMMARY OF THE INVENTION

A method of forming a generally leak-proof peripherally sealed absorbent pad and a pad formed by such method are disclosed herein. Non-sealed layered pads are formed by assembling the following layers: (1) a sheet of liquid-impermeable material; (2) bibulous pads disposed on the sheet of liquid-impermeable material, the bibulous pads disposed relative to each other based on a predetermined spacing; (3) a liquid-permeable sheet disposed on top of the bibulous pads; and (4) a sheet of liquid-impermeable material having precut apertures disposed on the liquid-permeable sheet, the apertures sized and shaped to be framed by the pads and spaced relative to each other based on the predetermined spacing. The non-sealed layered pads are then sealed along a periphery of the precut apertures to the sheet of liquid-impermeable material to form a sheet of absorbent pads. The sheet of absorbent pads are then cut proximate sealed edges of the precut apertures to form a plurality of generally leak-proof peripherally sealed absorbent pads.

A conveyor belt may be used for assembling the layers of the non-sealed layered pad.

The non-sealed layered pads may be sealed using heat sealing, sonic welding or adhesive bonding.

The liquid-impermeable sheet and/or liquid-impermeable sheet having a precut apertures may be made of a plastic film material.

The liquid-permeable sheet may be made of an absorbent paper. The absorbent paper may be an air laid material.

The pads are wrapped/sealed along all of the edges of the pad which allows absorption to occur in a vertical plane while preventing gravity induced overflow with spillage/leakage along the dependent margin. The peripherally sealed absorbent pad is ideal for bandages (which can be worn by ambulatory patients) and table sheets, such as a surgery table drip pad.

The peripherally sealed absorbent pad may be used to topically apply chemicals. The peripherally sealed absorbent pad may be used as a pre-moistener. The peripherally sealed absorbent pad may be used for burn care. The peripherally sealed absorbent pad may be used to apply anti-microbial and/or other beneficial or therapeutic pharmaceutical agents.

Other uses for the pad include packaging of poultry for the absorption of poultry juice.

BRIEF DESCRIPTION OF THE DRAWINGS

These as well as other features of the present invention will become more apparent upon reference to the drawings wherein:

FIG. 1 is a perspective view showing a process of forming an absorbent pad using a precut overlay;

FIG. 2 is a top view showing two pads (prior to cutting to separate the two pads) formed using the method shown in FIG. 1;

FIG. 3 is a cross section view of an absorbent pad taken along line 3—3; and

DETAILED DESCRIPTION OF THE INVENTION

Figure 4:
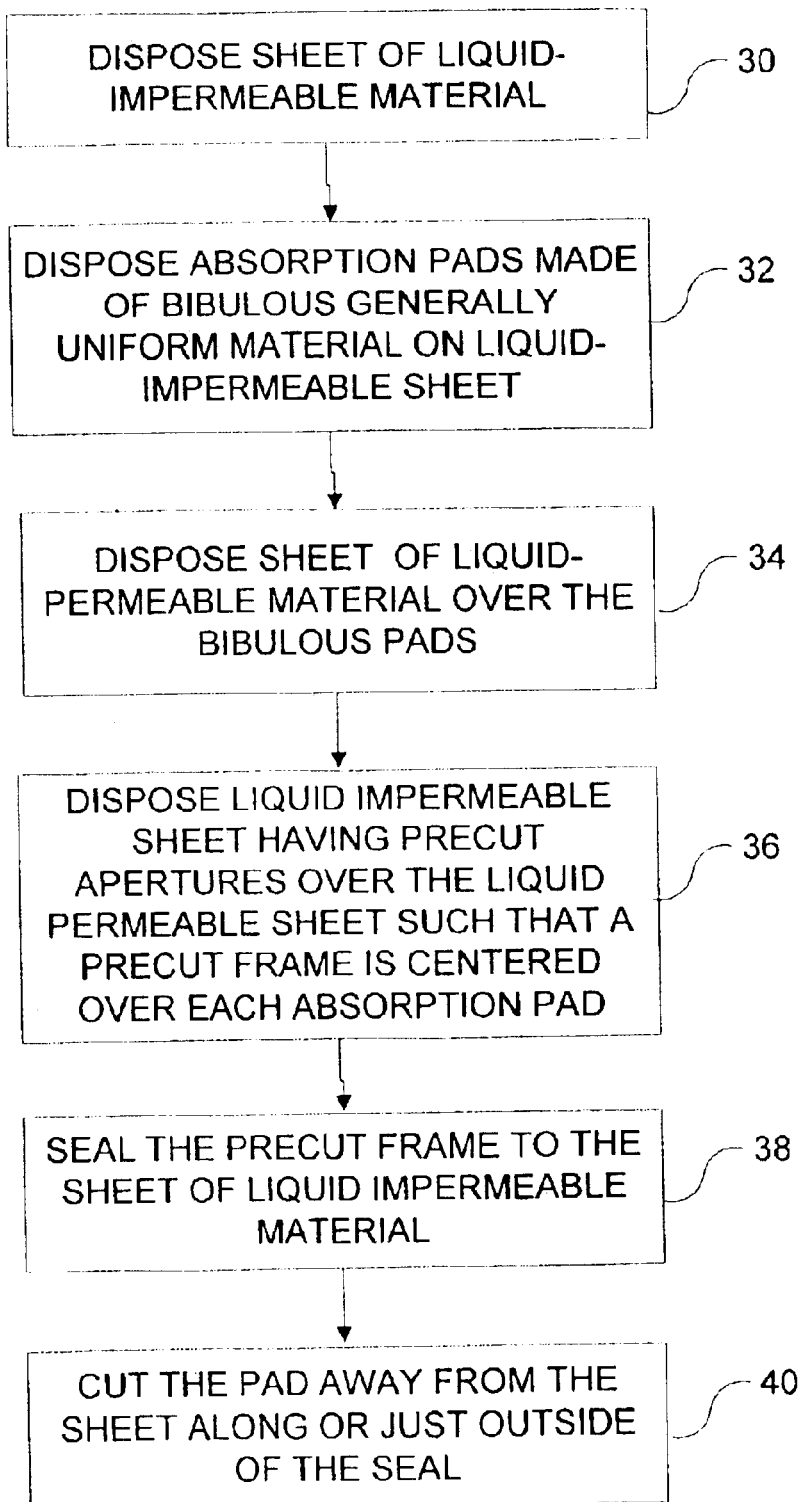
FIG. 4 is a flow diagram showing a process of forming an absorbent pad using a precut overlay as shown in FIG. 1.

A method of forming generally leak-proof peripherally sealed absorbent pad using a precut overlay is shown and described herein. Using precut overlays eliminates the manual procedure of wrapping the liquid-impermeable sheet around the bibulous layer to form a frame around the liquid-permeable sheet.

The exemplary generally leak-proof peripherally sealed absorbent pad described herein in described with reference to a compression sponge for wound care. In particular, the exemplary generally leak-proof peripherally sealed absorbent pad is described with reference to a compression sponge used for recovery from a tumescent liposuction procedure. The pad is sealed along the periphery, i.e., it is sealed around all of the edges of the pad, which allows the pad to be used in a vertical orientation while preventing gravity induced overflow with spillage/leakage along the dependent margin. Thus, the pad is ideally suited for use as a bandage for an ambulatory patient, such as a patient recovering from tumescent liposuction. However, as described in further detail later, it will be appreciated that the peripherally sealed absorbent pad and method of making same described herein can be used for many other applications in the medical field as well as many non-medical applications.

Referring now to the drawings wherein the showings are for purposes of illustrating preferred embodiments of the present invention only, and not for purposes of limiting the same, FIG. 3 illustrates an exemplary generally leak-proof peripherally sealed absorbent pad 10, e.g., compression sponge for placement at a wound site on the skin of a person. The generally leak-proof peripherally sealed absorbent pad 10 is formed using a precut overlay 20.

The pad 10 has a lower cover sheet 14 which is in contact and interfaces with the skin when the pad 10 is in use, and is constructed of conventional absorbent paper through which liquid can pass. Preferably, the paper 14 is air laid paper. The cover sheet 14 can be provided with small pieces of double-faced adhesive (not shown) for adhesion of the pad 10 to wound-site skin if that skin is not too sensitive for such adhesive action. Otherwise, the pad 10 can be provided without adhesive pieces and can be retained in place with adhesive tape strips applied externally, with a dressing-covering, with a tight-fitting overlay elastic garment, or with any other appropriate retainer as would be recognized in the art. The post-treatment of liposuction procedures on a patient can be effectively accomplished by applying pad(s) 10 at the site(s) of liquid drainage and then having the patient wear an elastic garment (not shown) over the pad(s) 10. Because of the characteristics of the layer 12, described below, with respect to generally uniform distribution of absorbed liquid therein, pressure generated by the elastic garment against the pad 10 likewise is generally uniformly distributed to thereby reduce the potential for bruising of affected skin of the patient during liquid drainage.

Immediately behind the sheet cover 14 of absorbent paper is a bibulous layer 12 constructed of a thickness of conventional super absorbent woven fibers networked to draw liquid in wick-like fashion to thereby quickly distribute absorbed liquid generally uniformly. The layer 12 can be provided with an antibacterial agent to prevent organism growth. Physical configuration of the surface of the layer 12 can be smooth which aids in preventing bruising as earlier noted, or it can be of a pattern such as a waffle or other design which may be more comfortable and provides for better air circulation for sensitive wounds such as those suffered by burn victims. Depending upon the requirements of treatment for particular wounds, various thicknesses of layer 12 can be provided to include different characteristics with respect to porosity, density, reservoir capacity, and the like.

Immediately behind the bibulous layer 12 is an outer surface of generally formless pliable plastic film 16 that is impervious to liquid passage. As best seen in FIGS. 1 and 3, a sheet 18 having precut apertures 20 is immediately in front of the cover sheet 14. The sheet 18 is also a generally formless pliable plastic film that is impervious to liquid. The liquid-impermeable sheet 18 having apertures 20 and the liquid-impermeable outer surface 16 are sealed together along all of the edges using any of the methods known in the art, for example, heat sealing, sonic welding, adhesive bonding, etc. Such construction (scaling along the entire periphery, i.e., all edges) can alleviate liquid leakage from the perimeter of the pad 10.

In use, the pad 10 is placed over a wound, and can be held in place by an overlaying elastic garment (not shown), by adhesive tape strips (not shown) bridging from the pad to surrounding skin, by adhesive double-faced tape pieces (not shown) applied minimally as described above, or by any other dressing method as recognized in the art. Thus, if the pad is used to treat the site of a burn, minimal or no adhesive material is used, and the pad is held in place in any manner that a physician determines as most comfortable for a patient. The pads 10 have special utility in the treatment of liposuction recovery where favorable tumescent methodology has been employed. Because this methodology includes sub-cutaneous infusion of a large quantity of liquid which must be expelled after the liposuction procedure is completed, the high reservoir capacity and wicking action found in the pads beneficially accomplish liquid removal directly from skin sites where liposuction has been performed by retaining pads 10 in place with a tight-fitting elastic garment. Because the pad 10 has sealed edges, it is especially amenable to use under a garment since no leakage occurs from the edges of the pad 10 while a user moves about in normal activities. Absorbed liquid rapidly travels throughout the layer 12 because of wicking action to thereby provide a generally uniformly pressure-reactant pad 10 throughout which externally applied pressure, such as by an elastic garment, is uniformly distributed throughout the pad 10 to thereby evenly distribute such pressure to the patient while accomplishing reduced bruising and effective drainage control. Because one or more pads 10, as needed, effectively draw weeping liquid away from a wound site while providing a generally uniform pressure in accord with pressure generated by an external source at one area of the pad 10, the pads 10 enhance comfort, convenience and healing.

An exemplary process of forming a generally leak-proof peripherally sealed absorbent pad described above is shown schematically in FIG. 1 and as a block diagram in FIG. 4. The pad is formed by layering the various materials and then sealing and cutting the pads as described above. FIG. 1 illustrates the various layers being assembled and then put together by feeding the layers through two large rollers. It will be appreciated that various known in the art can be used for assembly of the layers. For example, the layers may be assembled using a conveyor belt.

The first sheet in the process of assembling the layers is a sheet of liquid-impermeable material 16 (outer surface) (block 30). The sheet may be disposed on a manufacturing device, such as a conveyor belt. A plurality of pads 12 made of a generally uniform bibulous material are disposed on the impermeable sheet 16 (block 32). The bibulous pads 12 are precut to a desired size and shape based on the intended application of the pads 10. The pads are spaced apart at a predetermined distance. The predetermined distance allows sufficient space for sealing and cutting the pads as described below without having an excess amount of materials therebetween. A layer formed of a liquid-permeable material 14 (lower cover sheet) is disposed on the bibulous pads 12 (block 34).

A sheet formed of a liquid-impermeable material 18 and having precut apertures 20 is disposed on the liquid-permeable layer 14 such that the liquid-permeable material is framed by liquid-impermeable material (block 36). The apertures are sized and shaped based on the size and shape of the bibulous pads 12. The apertures should be of the same shape as the pad, but slightly smaller than the pad such that a border or frame of the pad surrounds the periphery of the aperture. The apertures are spaced apart using predetermined spacing relative to the predetermined spacing for the pads so that the apertures 20 are properly centered about the bibulous pads 12.

The layer of materials as described above and shown in the Figures are then sealed (block 38). The exemplary pad 10 shown is rectangular in shape (although other shapes could be used). The pad 10 is sealed along all of the edges. In the rectangular example shown, the pad has four edges forming the perimeter or periphery of the pad 10. All of the edges forming the perimeter or periphery of the pad are sealed. Various techniques may be used to seal the pads. For example, the pads may be heat sealed, sonically sealed or sealed using an adhesive. After the sealing, there are a plurality of connected pads, as shown in FIGS. 1 and 2. The pads are then cut (e.g., along line 22) such that a plurality of sealed pads 10, such as the one shown in FIG. 3 are formed.

While the present invention described herein is ideally suited for the manufacturing of absorbent pads for use in medical applications, such as patient recovery from tumescent liposuction procedures, it will be appreciated that the present invention can be applied to a variety of applications. Such applications include sterile uses as well as non-sterile uses. Examples of sterile uses include, but are not limited to wound care (e.g., sponges), table pads, such as surgery table pads, pads containing chemicals for topical applications. (e.g., anti-microbial pads, for example for use in burn care or pads containing other beneficial or therapeutic pharmaceutical agents) and pre-moistened pads (e.g., face moisturizers, hand lotions, etc.). The pads can also be used for non-medical/health-care applications. One example of such non-medical use is the packaging of poultry, such as chicken. Packaged poultry typically includes a sponge for absorbing juice from the poultry.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. A method of forming a generally leak-proof peripherally sealed absorbent pad, the method comprising:
   forming a plurality of non-sealed layered pads by assembling layers comprising:
      a sheet of liquid-impermeable material;
      a plurality of bibulous pads disposed on the sheet of liquid-impermeable material, the bibulous pads disposed relative to each other based on a predetermined spacing;
      a liquid-permeable sheet disposed on top of the plurality of absorption pads; and
      a sheet of liquid-impermeable material having a plurality of precut apertures disposed on the liquid-permeable sheet, the apertures sized and shaped to be framed by the bibulous pads and spaced relative to each other based on the predetermined spacing;
   sealing the plurality of non-sealed layered pads along a periphery of the precut apertures to the sheet of liquid-impermeable material to form a sheet of absorbent pads; and
   cutting the sheet of absorbent pads proximate sealed edges of the precut apertures forming a plurality of generally leak-proof peripherally sealed absorbent pads.

2. The method of claim 1, wherein a conveyor belt is used for assembling the layers of the non-sealed layered pads.

3. The method of claim 1, wherein sealing the plurality of non-sealed layered pads comprises heat sealing the plurality of non-sealed layered pads.

4. The method of claim 1, wherein sealing the plurality of non-sealed layered pads comprises sonic welding the plurality of non-sealed layered pads.

5. The method of claim 1, wherein sealing the plurality of non-sealed layered pads comprises adhesively bonding the plurality of non-sealed layered pads.

6. The method of claim 1, wherein the outer layer is made of a plastic film material.

7. The method of claim 6, wherein the precut frame is made of a plastic film material.

8. The method of claim 1, wherein the precut frame is made of a plastic film material.

9. The method of claim 1, wherein the liquid-permeable sheet is made of an absorbent paper.

10. The method of claim 9, wherein the liquid-permeable sheet is made of an air laid material.

11. The method of claim 1, wherein a respective generally leak-proof peripherally sealed absorbent pad is used for wound care.

12. The method of claim 11, wherein the respective generally leak-proof peripherally sealed absorbent pad is used for patient recovery from a tumescent liposuction procedure.

13. The method of claim 1, wherein a respective generally leak-proof peripherally sealed absorbent pad is used as a surgery table drip pad.

14. The method of claim 1, wherein a respective generally leak-proof peripherally sealed absorbent pad is used to topically apply chemicals.

15. The method of claim 1, wherein a respective generally leak-proof peripherally sealed absorbent pad is used as a pre-moistener.

16. The method of claim 1, wherein a respective generally leak-proof peripherally sealed absorbent pad is used for burn care.

17. The method of claim 16, wherein the respective generally leak-proof peripherally sealed absorbent pad is used to apply an anti-microbial.

18. The method of claim 1, wherein a respective generally leak-proof peripherally sealed absorbent pad is used to absorb poultry juice.

19. A sealed absorbent pad produced according to the process of claim 1.

* * * * *